United States Patent [19]

Degen

[11] 4,331,142
[45] May 25, 1982

[54] CUFFED TRACHEAL TUBE

[75] Inventor: Peter J. Degen, Dayton, Ohio

[73] Assignee: Riverain Corporation, Dayton, Ohio

[21] Appl. No.: 109,370

[22] Filed: Jan. 3, 1980

[51] Int. Cl.³ .......................................... A61M 16/00
[52] U.S. Cl. ............................. 128/207.15; 128/349 R
[58] Field of Search .................... 128/349, 351, 207.15

[56] References Cited

U.S. PATENT DOCUMENTS

| | | | |
|---|---|---|---|
| 3,292,627 | 12/1966 | Harautuneian | 128/349 |
| 3,734,100 | 5/1973 | Walker et al. | 128/207.15 |
| 4,003,382 | 1/1977 | Dyke | 128/349 |
| 4,116,201 | 9/1978 | Shah | 128/351 |

OTHER PUBLICATIONS

Hackh's Chemical Dictionary, p. 82, 3rd edition.
Modern Plastics Encyclopedia, pp. 188–189, 1963.
Zimmerman, Handbook of Trade Names, pp. 108–109, 1965.

*Primary Examiner*—Robert W. Michell
*Assistant Examiner*—Nancy A. B. Swisher
*Attorney, Agent, or Firm*—Biebel, French & Nauman

[57] ABSTRACT

An improved tracheal tube cuff which is resistant to gas permeation. The improved cuff has good compliance and has a nitrous oxide permeability of less than 10,000 cc/mil/100 sq. in/24 hrs/atms of 100% nitrous oxide. The preferred cuff material is a cross-linked, polyester-based polyurethane resin.

8 Claims, 1 Drawing Figure

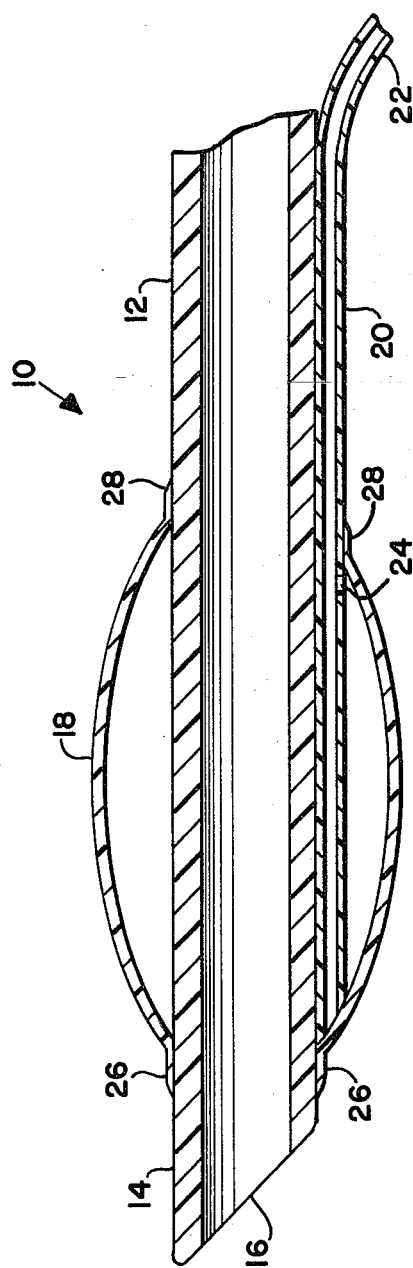

CUFFED TRACHEAL TUBE

BACKGROUND OF THE INVENTION

The present invention relates to cuffed endotracheal and tracheostomy tubes (both referred to generally as tracheal tubes) or other types of cuffed tubes which encounter absorptive gases. More particularly, it relates to a tracheal tube having a cuff resistant to absorption of nitrous oxide anesthetic gas.

There are many types of cuffed tubes and catheters for use as medical devices. These include tracheal tubes, Foley catheters, Dennis tubes, rectal catheters, etc. However, tracheal tubes encounter conditions and demand characteristics which are unique. One of the most crucial distinctions is the fact that tracheal tube cuffs, unlike other types of medical tubes, are subjected to anesthetic gases.

Tracheal tubes are used to provide an air-way through the trachea into the lungs of a patient during respirator therapy or general anesthesia. During anesthesia, such tubes allow nitrous oxide and other gases to be administered to the patient in controlled amounts with the tube remaining in the desired location and with the trachea sealed off by the inflated cuff.

The inflatable cuff should provide both airway seal during positive-pressure ventilation and protection from aspiration without causing significant trauma to the trachea. A serious practical dilemma exists because lateral wall pressure adequate to maintain tracheal seal may decrease or eliminate capillary flow in the lamina propria, and cuff-to-trachea pressure that permits capillary flow may also permit gas leak and/or aspiration. In regard to the latter, studies have been done to determine the minimum intra-cuff pressure needed to prevent tracheal aspiration of dye in anesthestized patients whose tracheas are intubated. See, for example, Bernhard et al, "Adjustment of Intracuff Pressure to Prevent Aspiration," *Anesthesiology*, Vol. 50, p. 363+ (April 1979).

Thus, the recommended procedure has been to carefully adjust the cuff pressure to a point where an adequate tracheal seal is maintained without overinflating the cuff and, thereby, damaging the walls of the trachea.

It is also usually recommended that the newer high volume-low pressure cuffs be used to further aid in preventing tracheal wall damage. See, "Tracheal Tubes", *Health Devices*, Vol. 7, p. 75+ (Jan. 1978). That article looked at the three general types of tracheal tube cuffs. These are (1) low volume-high pressure cuffs, (2) intermediate cuffs which will tend to seal like high volume-low pressure types if used in relatively narrow tracheas, but which require extra pressure in relatively wide tracheas, and (3) high volume-low pressure cuffs. A thin (around 3-15 mil) soft polyvinyl chloride was used to produce most of the high volume-low pressure cuffs tested in that article.

The *Health Devices* article goes on to warn, however, that since higher volume cuffs are generally thinner, they are more vulnerable to inward diffusion of nitrous oxide. Thus, the increased use of low pressure cuffs has brought attention to this recognized problem.

A study reported in Stanley, "Nitrous Oxide and Pressure and Volumes of High and Low-pressure Endotracheal-tube Cuffs in Intubated Patients," *Anesthesiology*, Vol. 42, p. 637+ (May 1975) indicates that cuff overexpansion during anesthesia may be an important cause of tracheal or laryngeal trauma and postoperative sore throat in patients whose tracheas have been intubated. This overexpansion was attributed to diffusion of nitrous oxide into the cuff and slow diffusion of nitrogen out.

A more recent study demonstrates that gas volumes in most cuffs increase 1.7 to 7 ml after 30 minutes of exposture to 100 percent nitrous oxide. This is reported in Bernhard et al, "Physical Characteristics of and Rates of Nitrous Oxide Diffusion into Tracheal Tube Cuffs," *Anesthesiology*, Vol. 48, p. 413+ (June 1978).

In view of this result, an additional procedure is recommended. As stated in the 1978 *Anesthesiology* article:

It is difficult to know how porous for nitrous oxide a cuff is just by looking at it. One should, therefore, assume nitrous oxide diffusion if the cuff was inflated with air, and deflation to a "safe" intracuff pressure should be carried out approximately every 30 minutes.

It would clearly be better to avoid the need for such adjustments. Accordingly, a number of proposals have been made which would do this. These can be conveniently divided into two categories: (1) use of cuff pressure regulating devices and (2) use of filled cuffs which have less tendency to absorb nitrous oxide gases. An example of use of valves as inflation control devices in preventing undue cuff pressures is found in Shan U.S. Pat. No. 4,116,201 and Wallace U.S. Pat. Nos. 4,018,231 and 3,901,246. Examples of filled cuffs are found in U.S. Pat. Nos. 3,640,282 (sponge rubber filled cuff); 4,022,217 (liquid saline solution filled cuff); and 3,971,385 (silicone gel filled cuff).

The difficulty with such devices is that they are complex and expensive and were not specifically designed to overcome the problem of nitrous oxide diffusion in the first place. Accordingly, the need exists for a simple, inexpensive and yet effective means to prevent undue pressure rises in tracheal tube cuffs and other tube cuffs which are exposed to anesthetic gases.

SUMMARY OF THE INVENTION

The present invention meets that need by utilizing a cuff material which is resistant to gas permeation while at the same time having other properties desirable for a tracheal tube cuff. Generally, those additional properties are ones of softness or compliance in order to produce the low tracheal wall pressures. That is, the tracheal tube cuff of the instant invention enjoys all of the favorable characteristics of the best high volume-low pressure cuffs, without the major disadvantage of cuff overexpansion during anesthesia.

The preferred cuff material is a cross-linked, polyester-based polyurethane resin. The polyurethane is made up of hard segments and soft segments which control its properties including gas transmission. The hard segment has as its components a multifunctional isocyanate such as difunctional and polyfunctional aliphatic or aromatic isocyanates. Examples include 4,4'-diphenylmethane diisocyanate, methylene bis [4-cyclohexyl isocyanate], toluene diisocyanate, and isophorone diisocyanate, and a chain extender in the form of a low molecular weight diol such as a butanediol. The soft segment is provided by a difunctional polyester component such as polycaprolactone glycol, polyethylene adipate glycol, polypropylene adipate glycol, polylbutylene adipate glycol and other aliphatic macro-diols. Cross-linking is achieved by use of typical cross-linking agents such as trimethylolpropane, pentaerythritol, 1,2,3-propanetriol etc.

It is possible to vary these components and their amounts to produce cross-linked, polyester polyurethanes having various degrees of softness and resistance to gas permeability. A convenient scale used to determine gas permeability is cc diffusion per mil of wall thickness per 100 sq. inches of surface per 24 hours per atmosphere of driving pressure at 100% nitrous oxide. Using this scale, the tracheal tube cuffs of the present invention have a value of less than 10,000 and preferably less than 8,000. In fact, the especially preferred cuff has a permeability of less than 2000, namely around 1200–1300 cc/mil/100 sq. inch/24 hours/atms.

Cuff compliance is determined by a combination of modulus, elongation and tensile strength. The preferred cuff materials of the present invention have a Young's modulus of less than about 2000 and more preferably less than about 1200. The break elongation may range from around 100 to 700%, and prefer ably around 400–500%. The elongation set should be less than about 20%. Finally, the tensile strength should be greater than about 3000 psi, and preferably greater than about 5000 psi.

These compliance features will produce a cuff which will under normal inflation minimize damage to the walls of the trachea and yet will give a good seal which will prevent gas leaks or aspiration. More importantly, it will substantially reduce overinflation during use due to nitrous oxide gas absorption. It is also resistant to absorption of gases in addition to nitrous oxide including other anesthetic gases and oxygen. This eliminates the need to use complex and expensive pressure valve controls and filled cuffs and reduces the need for constant vigilance, or any of the other proposed means to avoid the problem of overexpansion because of gaseous diffusion into the cuff.

Accordingly, it is an object of the present invention to provide a cuffed tracheal tube which is resistant to gas permeation. These and other objects and advantages of the invention will become apparent from the following description, the accompanying drawing, and the appended claims.

BRIEF DESCRIPTION OF THE DRAWINGS

The FIGURE is a cross-sectional view of a portion of a tracheal tube of one embodiment of the present invention.

DESCRIPTION OF THE PREFERRED EMBODIMENTS

Referring to the FIGURE, there is shown one form of tracheal tube 10. The tracheal tube 10 includes a hollow plastic shaft 12 having a distal end 14 and a proximal end (not shown). The distal end 14 has an opening 16 for introducing anesthetic gas and other gases to the patient. That opening can be of the Magill type with an open end as shown or a Murphy type with an eye at the side of the distal end.

Adjacent distal end 14 is cuff 18 which is in communication with a lumen or gas passageway 20 extending along the length of shaft 12 and within the wall thereof until nearing the proximal end where a small tube 22 joins the integral gas passageway to an inflating means (not shown). Gas passageway 20 can be formed during extrusion of shaft 12 and a cut made for opening 24 within the cuff 18, all as is well known in the art. Alternatively, gas passageway 20 may be a separate lumen exterior to shaft 12, as is also well known in the art. In any event, the gas passageway 20 has one end communicating with the interior of cuff 18 for inflation and deflation thereof and the other end of tube 22 is adapted to receive the inflating means.

Shaft 12 may be made of a polyurethane material, but could be other plastics as well such as polyvinyl chloride, latex or silicone elastomer. Whatever the material used for shaft 12, it must be smooth, sufficiently flexible to minimize abrasion of tissue, and should preferably be transparent. The tracheal tube 10 should be sufficiently soft at body and room temperature to conform to the patient's anatomy without undue force. Shaft 12 terminates at the proximal end in a standard male connector (not shown) for attachement to the anesthetic or other gas supply. Cuff 18 is adhesively attached to shaft 12.

The cuff itself is the principal contribution of the present invention to the art. Thus, rather than going to extensive valve control means or filled cuffs to avoid undue pressure rises because of gas absorption, it is possible to avoid the problem by use of a cuff material resistant to gas permeation. A material which has been found to be particularly effective in that regard is a cross-linked, polyester polyurethane resin; although, other materials could also be developed having the necessary combination of properties. Those properties include resistance to gas permeation and sufficient compliance or softness.

The preferred polyurethane material has both hard and soft segments which contribute to produce this combination of properties. Basically, however, there are four major components: (1) a multifunctional isocyanate, preferably an aromatic diisocyanate, (2) a low molecular weight diol chain extender such as aliphatic or aromatic glycols, (3) a difunctional polyester diol, and (4) a cross-linking agent. The resulting reaction product is a cross-linked, polyester polyurethane resin.

The composition of the polymer is important since it has been found that even as closely a related material as a polyether polyurethane resin does not have sufficient resistance to nitrous oxide permeation. As an example, comparative polyurethanes were prepared with the same ingredients for components (1), (2) and (4). Thus, the multifunctional isocyanate used in each instance was 4,4'-diphenylmethane diisocyanate, the low molecular weight chain extender was 1,4-butanediol, and the cross-linking agent was trimethylolpropane. However, as the soft segment portion in run A used a polytetramethylene ether glycol--Polymeg 2000 from Quaker Oats Co.—a polyether component; whereas, runs B and C used a difunctional polyester material. In run B this was a polycaprolactone glycol—PCP-0240 from Union Carbide and in run C it was a polyethylene adipate glycol—Formrez from Witco Chemical Corp. Run A had a permeability to 100% nitrous oxide of 27,300 cc/mil/100 sq. in./24 hrs/atms; whereas, Run B had a permeability of 6900 and Run C had a permeability of only 1200. On this scale, it is desirable to have a permeability of less than 10,000 and preferably less than 8000. Runs B and C easily meet that criteria.

In addition, Run B had a Young's modulus of 620, a tensile strength of 5200 psi, a break elongation of 470%, and an elongation set of 2%. Run C had a Young's MOdulus of 820, a tensile strength of 5600 psi, a break elongation of 425% and an elongation set of 4%. These characteristics give the cuff a softness and compliance well within the earlier given ranges. They are also sufficient to match or best the compliance characteristics of most commercial tracheal tube cuffs.

More importantly, such materials are greatly superior to commercially available tracheal tube cuffs in terms of resistance to absorption of gases. As an example, the resistance to nitrous oxide was studied since absorption of such gases during anesthesia is a known cause of overinflation of tracheal tube cuff. This study was made by intubating dogs with endotracheal tubes under conditions identical to the use of these devices in humans. The dogs were selected so that the tracheas corresponded closely in size to the average human, adult trachea. Once intubated, artificial respiration was carried out with a standard respirator using the common mixture of 50% nitrous oxide and 50% oxygen. Ventilation was maintained for five hours with the endotracheal cuff pressures monitored during this period.

All devices evaluated were 8.0 mm size (standard for adult male) and had cuffs of similar configuarations. PVC(1) was a tracheal tube-high residual volume cuff from National Catheter Corp., PVC(2) was a similar tracheal tube from Portex, and PVC(3) was a 8 millimeter tracheal tube from Shiley. All utilize relatively a thin, 3 mil, 11 mil and 9 mil (respectively), polyvinyl chloride cuff. Runs B and C utilized 4 mil thick cuffs prepared of the same materials as Runs B and C described above. Run A was not tested in dog intubation because of its poor resistance to nitrous oxide gas permeation in the first place. The results are given in the table below:

TABLE

| Time in hours | Cuff Pressure in mmHg | | | | |
|---|---|---|---|---|---|
| | PVC(1) | PVC(2) | PVC(3) | Run B | Run C |
| 0 | 20 | 30 | 24 | 20 | 24 |
| 1 | 38 | 43 | 38 | 20 | 24 |
| 2 | 48 | 60 | 54 | 26 | 26 |
| 3 | 62 | 68 | 72 | 34 | 28 |
| 4 | 76 | 76 | 84 | 42 | 32 |
| 5 | 88 | 82 | 86 | 46 | 36 |

As can be seen, the tracheal tube cuffs of the present invention (Runs B and C) had superior resistance to anesthetic gas permeation. In use this should aleviate the problem of cuff overinflation due to absorption.

While the products herein described constitute preferred embodiments of the invention, it is to be understood that the invention is not limited to these precise products, and that changes may be made therein without departing from the scope of the invention which is defined in the appended claims.

What is claimed is:
1. A tracheal tube comprising

(a) an elongated shaft for extending into the trachea of a patient to deliver anesthetic and other gases into the lungs of the patient, said shaft having an outer surface and proximal and distal ends, (b) an inflatable 2–8 mil thick cuff mounted on the outer surface of said elongated shaft adjacent to said distal end, said cuff being made of a polyurethane material having as components a multifunctional isocyanate, a low molecular weight chain extender, a difunctional polyester diol and a cross-linking agent, said cuff having a nitrous oxide gas permeability of less than 10,000 cc/mil/100 sq. in/24 hrs/atms of 100% nitrous oxide.

said cuff also having a Youngs Modulus of less than about 2000, a tensile strength of greater than about 3000 psi, a break elongation of around 100–700% and an elongation set of less than about 20%, and (c) a gas passageway having one end communicating with the interior of said inflatable cuff and having the other end adapted to receive an inflating means for delivering gas to inflate said cuff.

2. The tracheal tube of claim 1 wherein said cuff has a nitrous oxide gas permeability of less than 8000 cc/mil/100 sq. in./24 hrs/atms of 100% nitrous oxide.

3. The tracheal tube of claim 2 wherein said cuff has a thickness of 3–6 mils.

4. The tracheal tube of claim 3 wherein said cuff has a Youngs Modulus of less than 1200, a tensile strength of greater than about 5000 and an elongation of around 400–500%.

5. The tracheal tube of claim 1 wherein said cuff has a nitrous oxide gas permeability of less than 2000 cc/mil/100 sq. in/24 hrs/atms of 100% nitrous oxide.

6. The tracheal tube of claim 1 wherein said multifunctional isocyanate is selected from the group consisting of 4,4'-diphenylmethane diisocyanate, methylene bis [4- cyclohexyl isocyanate], toluene diisocyanate, and isophorone diisocyanate, and said difunctional polyester is selected from the group consisting of polycaprolactone glycol, polyethylene adipate glycol, polypropylene adipate glycol, and polybutylene adipate glycol.

7. The tracheal tube of claim 1 wherein said low molecular weight chain extender is a butanediol and said cross-linking agent is trimethyolpropane.

8. The tracheal tube of claim 7 wherein said multifunctional isocyanate is 4,4'-diphenylmethane diisocyanate, said difunctional polyester is polyethylene adipate glycol and said low molecular weight chain extender is b 1,4-butanediol.

* * * * *